US011395617B2

(12) United States Patent
Li et al.

(10) Patent No.: US 11,395,617 B2
(45) Date of Patent: Jul. 26, 2022

(54) METHOD AND AN APPARATUS OF ACTIVELY SENSING NEURONAL FIRING FREQUENCY AT A FUNCTIONAL SITE IN A BRAIN

(71) Applicants: Xiaoping Li, Fukuoka (JP); Qian Xia, Fukuoka (JP); Jessica Li, Fukuoka (JP); Joanna Le Xi Li, Fukuoka (JP)

(72) Inventors: Xiaoping Li, Fukuoka (JP); Qian Xia, Fukuoka (JP); Jessica Li, Fukuoka (JP); Joanna Le Xi Li, Fukuoka (JP)

( * ) Notice: Subject to any disclaimer, the term of this patent is extended or adjusted under 35 U.S.C. 154(b) by 560 days.

(21) Appl. No.: 16/113,117

(22) Filed: Aug. 27, 2018

(65) Prior Publication Data

US 2019/0059760 A1 Feb. 28, 2019

Related U.S. Application Data

(60) Provisional application No. 62/578,463, filed on Oct. 29, 2017, provisional application No. 62/550,596, filed on Aug. 26, 2017.

(51) Int. Cl.
| | |
|---|---|
| *A61B 5/00* | (2006.01) |
| *A61N 2/02* | (2006.01) |
| *A61B 5/245* | (2021.01) |
| *A61N 2/00* | (2006.01) |
| *A61M 21/02* | (2006.01) |
| *A61B 5/0507* | (2021.01) |
| *A61M 21/00* | (2006.01) |

(52) U.S. Cl.
CPC ............ *A61B 5/245* (2021.01); *A61B 5/0507* (2013.01); *A61B 5/4064* (2013.01); *A61B 5/4824* (2013.01); *A61M 21/02* (2013.01); *A61N 2/006* (2013.01); *A61N 2/02* (2013.01); *A61B 2560/0223* (2013.01); *A61B 2562/0223* (2013.01); *A61M 2021/0055* (2013.01); *A61M 2021/0083* (2013.01); *A61M 2205/3317* (2013.01)

(58) Field of Classification Search
CPC .... A61N 2/00–12; A61B 5/4821–4824; A61B 5/4064; A61B 2562/0223; A61M 2205/3317
See application file for complete search history.

(56) References Cited

U.S. PATENT DOCUMENTS

| | | | | |
|---|---|---|---|---|
| 4,998,112 | A | * | 3/1991 | Franchi .................. G01R 29/10 342/360 |
| 6,828,937 | B1 | * | 12/2004 | Hilgeman ............. G01S 5/0221 342/357.64 |
| 2006/0161225 | A1 | * | 7/2006 | Sormann ............... A61N 1/3787 607/61 |

(Continued)

*Primary Examiner* — Thaddeus B Cox
(74) *Attorney, Agent, or Firm* — Nixon & Vanderhye P.C.

(57) ABSTRACT

The present application provides a method and an apparatus of actively sensing a neuronal firing frequency at a functional site in a brain, the method comprising: generating a varying electromagnetic field and acting a near field of the generated electromagnetic field on a targeted brain functional site; sensing the alteration of the electromagnetic field at the targeted brain functional site; and determining a variation frequency of the alteration of the electromagnetic field at the targeted brain functional site as the neuronal firing frequency at the targeted brain functional site.

11 Claims, 6 Drawing Sheets generating a varying electromagnetic field and acting a near field of the generated electromagnetic field on a targeted brain functional site — S701 sensing the alteration of the electromagnetic field at the targeted brain functional site — S702 determining a variation frequency of the alteration of the electromagnetic field at the targeted brain functional site as the neuronal firing frequency at the targeted brain functional site — S703

(56) References Cited

U.S. PATENT DOCUMENTS

| | | | |
|---|---|---|---|
| 2007/0003781 A1* | 1/2007 | de Rochemont | H05K 1/162 428/615 |
| 2008/0269851 A1* | 10/2008 | Deem | A61N 5/02 607/101 |
| 2013/0190599 A1* | 7/2013 | Wyeth | A61B 5/0522 600/409 |
| 2014/0243647 A1* | 8/2014 | Clark | A61B 5/4878 600/407 |
| 2016/0278687 A1* | 9/2016 | Xia | A61B 5/0507 |
| 2017/0189709 A1* | 7/2017 | Goldberg | A61N 2/006 |
| 2020/0107725 A1* | 4/2020 | Tyler | G01R 33/4814 |

* cited by examiner

```
┌─────────────────────────────────────────────────┐
│ generating an electromagnetic field with its power in  │ ──── S101
│     variation at the preset modulating frequency       │
└─────────────────────────────────────────────────┘
                         │
                         ▼
┌─────────────────────────────────────────────────┐
│ arranging the generated electromagnetic field near the │
│   brain such that the targeted brain functional site is│
│ within the range of the near field of the electromagnetic│
│       field, to polarize extracellular fluid at the brain│ ──── S102
│   functional site with the power of the electromagnetic │
│         field, such that a polarization density of the  │
│         extracellular fluid varies at the preset modulating│
│    frequency and neurons in the extracellular fluid are │
│  modulated to fire at the preset modulating frequency   │
└─────────────────────────────────────────────────┘
```

FIG. 1

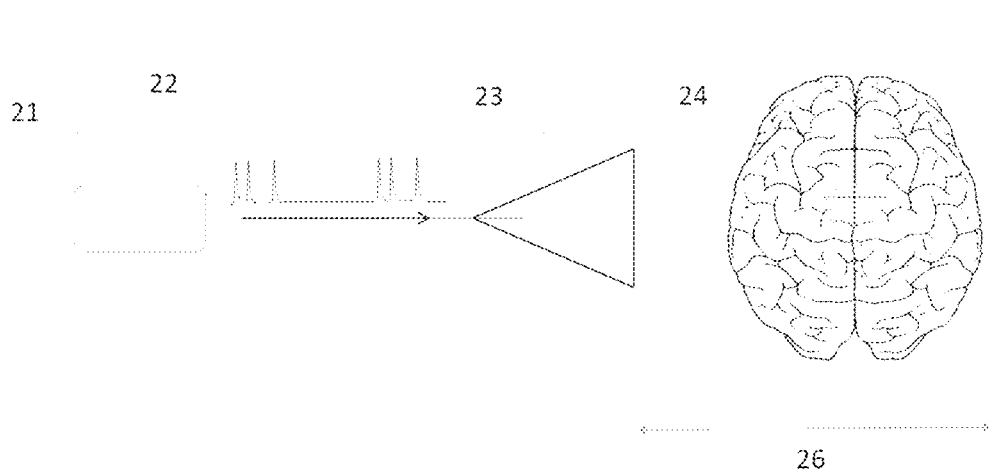

FIG. 2

METHOD AND AN APPARATUS OF ACTIVELY SENSING NEURONAL FIRING FREQUENCY AT A FUNCTIONAL SITE IN A BRAIN

RELATED APPLICATIONS

This application claims the benefit of priority under 35 USC § 119(e) of U.S. Provisional Patent Application No. 62/550,596 filed 26 Aug. 2017 and U.S. Provisional Patent Application No. 62/578,463 filed 29 Oct. 2017, the contents of which is incorporated herein by reference in their entirety.

TECHNICAL FIELD

The present application generally relates to a method and an apparatus of actively sensing a neuronal firing frequency at a functional site in a brain, in which an electromagnetic field is generated surrounding a brain and the activities in the brain depending on the neuronal firing frequencies are sensed by sensing the field interaction with the neuronal functional sites in the brain.

BACKGROUND

The brain is formed by neurons clustered into multiple functional sites. Each of the functional sites performs a particular function in the brain, and the functional activity of the functional site is characteristically related to the neuronal firing frequency at the functional site, showing as an activity in the brain. At each of the brain functional site, the neurons are surrounded by extracellular fluid that contains charged particles, such as calcium, potassium, and chloride. Each of the neurons has its gates on its semipermeable membrane for the charged particles in the extracellular fluid to flow in or out of the neuron. As the charged particles by diffusion flowing into and accumulating in the semipermeable membrane of the neuron and building up the membrane potential (i.e. polarization of the neuron) to a threshold value, when the membrane receives a stimulation, the gates on the membrane open for all the charged particles to flow out of the membrane (i.e. depolarization of the neuron), thereby completing a cycle of polarization and depolarization of the neuron. At the end of the depolarization, another cycle of polarization of the neuron starts towards the next depolarization, . . . and so on, forming the firing cycles of the neuron at a firing frequency characterizing the functional state of the brain functional site. For example, the firing frequency at the brain functional site for pain perception, e.g. anterior cingulate cortex (ACC), is related directly to the brain perception of pain. As the firing frequency of the ACC is below a certain value, there is no pain percept in the brain. As the firing frequency at the ACC is higher than a critical value, pain percept starts in the brain, and the pain percept gets more intense as the firing frequency increases.

As the charged particles in the extracellular fluid surrounding the neurons flowing into or out of the neurons by following the polarization and depolarization of the neurons periodically in the extracellular fluid, the concentration of the charged particles in the extracellular fluid changes accordingly. That is, the permittivity of the extracellular fluid as a dielectric material changes periodically following the polarization and depolarization cycle (i.e. the firing cycle) of the neurons in the extracellular fluid, and as the neurons in a functional site in the brain are synchronized in carrying out a function at the functional site, the firing frequency of the neurons is synchronized and the variation frequency of the permittivity of the extracellular fluid surrounding the neurons follows the neuronal firing frequency at the functional site. By measuring the variation frequency of the permittivity of the extracellular fluid surrounding the neurons, the neuronal firing frequency at the brain functional site is measured.

SUMMARY

In another aspect of the present invention, for actively sensing the neuronal firing frequency at a brain functional site, a varying electromagnetic field, including alternating and pulse electromagnetic fields, is generated through an antenna which is placed near the brain such that the targeted functional site of the brain is within the near field of the generated electromagnetic field.

Particularly, there is provided a method of actively sensing a neuronal firing frequency at a functional site in a brain, comprising:

generating a varying electromagnetic field and acting a near field of the generated electromagnetic field on a targeted brain functional site;

sensing the alteration of the electromagnetic field at the targeted brain functional site; and determining a variation frequency of the alteration of the electromagnetic field at the targeted brain functional site as the neuronal firing frequency at the targeted brain functional site.

Here the near field is defined by the distance d of the generated varying electromagnetic field from the antenna, the largest dimension D of the antenna, as well as the wavelength λ of the electromagnetic field generated by the antenna in vacuum in the following relationship:

$$0 < d \leq 0.62 * \sqrt{\frac{D^3}{\lambda}}$$

For example, in the case of selectively modulating the sleep promoting site ventrolateral preoptic nucleus (VLPO) in the brain, given that the dimension of the VLPO is about 1 cm and an electromagnetic field of 6 cm wavelength in vacuum will have a wavelength of 1 cm in the brain, the 1 cm wavelength matches the dimension of the VLPO for high modulation efficiency. In this case, the wavelength λ of the electromagnetic field is 6 cm and thus the frequency of the electromagnetic field is 5 GHz, and the largest dimension D of the antenna is 18 cm, then $$0 < d \leq 0.62 * \sqrt{\frac{18^3}{6}} = 19.3 \text{ cm}$$

That is, the maximum distance of the near field is 19.3 cm from the antenna. Here, the value of the dimension D relates to the value of the distance d, and those skilled in the art knows proper adjustment of the values of D and d correlatively to properly acting the targeted brain functional site.

Through the strong inductive and capacitive effect of the currents and charges in the antenna, the near field of the generated electromagnetic field induces the neuronal clusters formed by groups of neurons in the brain to act as the secondary antennas, thereby inducing an electric field in the brain, which polarizes the extracellular fluid in the targeted brain functional site. As a result of polarization of the extracellular fluid in the targeted brain functional site by the near field, the power of the near field is taken by the extracellular fluid in the targeted brain functional site in building the polarization density of the extracellular fluid, and the phase and amplitude of the waves of the electromagnetic field, including the near field, are altered, with the level of alteration depending on the level of the polarization density of the extracellular fluid, which varies with the concentration of the charged particles in the extracellular fluid. At the meantime, the neurons in the extracellular fluid at the brain site fire at a certain frequency, thereby varying the concentration of the charged particles in the extracellular fluid at the neuronal firing frequency and thus varying the polarization density of the extracellular fluid at the neuronal firing frequency, such that the alteration of the phase and amplitude of the waves of the electromagnetic field in the brain, including the near field, varies at the neuronal firing frequency relative to the generated electromagnetic field.

In the present invention, the neuronal firing frequency at a brain functional site is actively sensed with the generated varying electromagnetic field having its near field surrounding the targeted brain functional site and polarizing the extracellular fluid at the brain functional site, and by measuring the variation frequency of the alteration of the electromagnetic field in association with the variation of the polarization density of the extracellular fluid at the brain functional site, in which the polarization density of the extracellular fluid is induced by the electromagnetic field and is varied by the firing of the neurons at the brain functional site through varying the concentration of the charged particles in the extracellular fluid. By using a predetermined calibration of the sensed frequency in relation to the state or characteristics of the targeted brain functional site, the functional activity at the targeted brain functional site is sensed. In the method of the present invention, the frequency of the generated electromagnetic field in vacuum is in the range of 200 MHz to 150 GHz, with the optimum as such that the wavelength of the generated electromagnetic field in the brain matches the dimension of the targeted brain functional site. The measurement for the variation frequency of the alteration of the electromagnetic field, in which the alteration of the electromagnetic field is a result of its polarization of the extracellular fluid and as the charged particle concentration distribution of the extracellular fluid varies with the neuronal firing the alteration of the electromagnetic field varies, in association with the variation of the polarization density of the extracellular fluid at the brain functional site includes measuring the variation of the alteration of the phase of the sensed electromagnetic field (relative to the generated electromagnetic field) in association with the variation of the polarization density of the extracellular fluid at the brain functional site, and/or includes measuring the variation of the alteration of the amplitude of the sensed electromagnetic field (relative to the generated electromagnetic field) in association with the variation of the polarization density of the extracellular fluid at the brain functional site. Thus the measured variation frequency of the alteration is the neuronal firing frequency at the brain functional site.

Preferably, the frequency of the generated varying electromagnetic field in vacuum is such that the wavelength of the electromagnetic field at the brain functional site matches the dimension of the targeted brain functional site.

The waveform of the varying electromagnetic field may be any waveform, including but not limited to alternating waveform and pulse waveform.

The alteration of the electromagnetic field in the targeted brain functional site may be a phase alteration and is determined by comparing the phase of the sensed electromagnetic field at the brain functional site with the phase of the generated electromagnetic field, or the alteration of the electromagnetic field in the targeted brain functional site is an amplitude alteration and is determined by comparing the amplitude of the sensed electromagnetic field at the brain functional site with the amplitude of the generated electromagnetic field.

The alteration of the electromagnetic field at the targeted brain functional site may be sensed by the antenna or alternatively by an antenna separate from the antenna that generates the electromagnetic field acting on the brain functional site.

The functional site in the brain may be, for example, the anterior cingulate cortex (ACC) for pain perception, and the degree of pain percept in the brain is determined from the determined neuronal firing frequency at the ACC together with a calibration between the neuronal firing frequency and an intensity of pain.

The functional site in the brain may be, for example, the brain site for intention to act, including the prefrontal cortex and motor cortex.

In a further aspect of the present invention, there is provided an apparatus of actively sensing a neuronal firing frequency at a functional site in a brain, comprising a signal generation module, an antenna connected to the signal generation module, and a computing module, wherein, the signal generation module is configured to generate and send a varying current signal to the antenna for generating a varying electromagnetic field, a near field of which is used for acting on a targeted brain functional site;

the antenna is further configured to sense the alteration of the electromagnetic field at the targeted brain functional site, or the apparatus further comprises a separate antenna configured to sense the alteration of the electromagnetic field at the targeted brain functional site;

the computing module is configured to determine, based on the sensed alteration of the electromagnetic field at the targeted brain functional site, a variation frequency of the alteration of the electromagnetic field at the targeted brain functional site as the neuronal firing frequency at the targeted brain functional site.

The near field is defined by the distance d of the generated varying electromagnetic field from the antenna generating the electromagnetic field, the largest dimension D of the antenna, as well as the wavelength $\lambda$ of the generated electromagnetic field in vacuum in the relationship of $$0 < d \le 0.62 * \sqrt{\frac{D^3}{\lambda}}.$$

The frequency of the generated varying electromagnetic field in vacuum is such that the wavelength of the electromagnetic field at the brain functional site matches the dimension of the targeted brain functional site.

The waveform of the varying electromagnetic field is alternating or pulsed.

The alteration of the electromagnetic field in the targeted brain functional site may be a phase alteration and is determined by comparing the phase of the sensed electromagnetic field at the brain functional site with the phase of the generated electromagnetic field, or the alteration of the electromagnetic field in the targeted brain functional site may be an amplitude alteration and is determined by comparing the amplitude of the sensed electromagnetic field at the brain functional site with the amplitude of the generated electromagnetic field.

With the above solutions, the neuronal firing frequency at the targeted brain functional site can be easily determined and hence the brain activities can be determined with reference to the predetermined calibration of the sensed frequency in relation to the state or characteristics of the targeted brain functional site.

As would be appreciated by those skilled in the art, the advantages achieved by the above method can also be achieved by the above apparatus.

BRIEF DESCRIPTION OF DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic diagram showing a method of modulating a neuronal firing frequency at a brain functional site in a brain according to an embodiment of the present invention.

FIG. 2 schematically shows an apparatus of modulating a neuronal firing frequency at a brain functional site in a brain, in which a signal generation module generates and sends an electrical signal, e.g. a current signal with its amplitude modulated at a low frequency, to an antenna to generate an electromagnetic field with its near field acting on the brain to transform the brain from its wake mode to its sleep mode, according to an embodiment of the present invention.

DETAILED DESCRIPTION OF THE INVENTION

Figure 3:
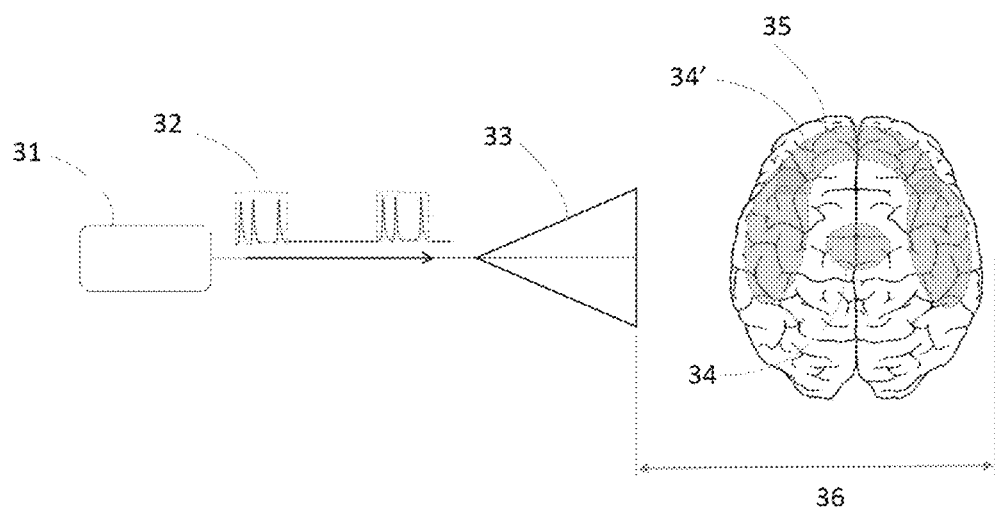
FIG. 3 schematically shows an apparatus of modulating a neuronal firing frequency at a brain functional site in a brain, in which a signal generation module generates and sends a series of electrical signals, e.g. current signals with its amplitude modulated at low frequencies, to an antenna to generate an electromagnetic field with its near field acting on the brain to facilitate the brain in its process of cleaning accumulated waste in the brain as well as completing the consumption of left over proteins surrounding the neurons for purposes of treatment and prevention of Alzheimer's disease, according to another embodiment of the present invention.

Some embodiments of the present invention will be described hereinafter with reference to the accompanying drawings.

Modulating of Neuronal Firing Frequency

For better understanding of the invention, modulating of neuronal firing frequency is first described below with reference to FIGS. 1-6.

In an embodiment, as shown in FIG. 1, a method of modulating a neuronal firing frequency at a brain functional site in a brain includes:

Step S101 of generating an electromagnetic field with its power in variation at the preset modulating frequency; and Step S102 of arranging the generated electromagnetic field near the brain such that the targeted brain functional site is within the range of the near field of the electromagnetic field, to polarize extracellular fluid at the brain functional site with the power of the electromagnetic field, such that a polarization density of the extracellular fluid varies at the preset modulating frequency and neurons in the extracellular fluid are modulated to fire at the preset modulating frequency.

The near field of the electromagnetic field may be generated by an antenna and satisfy the condition of $$0 < d \le 0.62 * \sqrt{\frac{D^3}{\lambda}},$$

wherein d represents the distance from the antenna to an edge of the near field where the near field ends, D represents the largest dimension of the antenna, and λ represents the wavelength of the generated electromagnetic field in vacuum. Here, given that d satisfies the above condition, the electrical power from the antenna can be effectively transferred onto the targeted brain functional site within the near field through the inductive and capacitive effect of the current and charges in the antenna applied on the targeted brain functional site via the neuronal clusters formed by groups of neurons in the brain, which act as the secondary antennas for receiving the electrical power from the antenna to the targeted brain functional site within the near field.

As the brain is surrounded by the near field of the electromagnetic field generated by the antenna, through the strong inductive and capacitive effect of the currents and charges in the antenna, the neuronal clusters formed by groups of neurons in the brain act as the secondary antennas to receive the power from the antenna deep into the brain regions within the near field.

Here the near field is limited by the distance d from the antenna, the largest dimension D of the antenna, as well as the wavelength λ of the electromagnetic field generated by the antenna.

The wavelength λ of the generated electromagnetic field in vacuum is such that the wavelength of the generated electromagnetic field at the brain functional site matches the dimension of the brain functional site. In this way, the brain functional site can be efficiently modulated by the electromagnetic field.

Additionally or alternatively, the wavelength λ of the generated electromagnetic field in vacuum may be such that the wavelength of the electromagnetic field at the brain functional site is from 70% to 130% of the dimension of the brain functional site.

For example, in the case of selectively modulating the sleep promoting site ventrolateral preoptic nucleus (VLPO) in the brain, given that the dimension of the VLPO is about 1 cm and an electromagnetic field of 6 cm wavelength in vacuum will have a wavelength of 1 cm in the brain, the 1 cm wavelength matches the dimension of the VLPO for high modulation efficiency. In this case, the wavelength λ of the electromagnetic field is 6 cm and thus the frequency of the electromagnetic field is 5 GHz, and the largest dimension D of the antenna is 18 cm, then $$0 < d \le 0.62 * \sqrt{\frac{18^3}{6}} = 19.3 \text{ cm}$$

That is, the maximum distance of the near field is 19.3 cm from the antenna. Here, the value of the dimension D relates to the value of the distance d, and those skilled in the art knows proper adjustment of the values of D and d correlatively to properly acting the targeted brain functional site.

In the present embodiment, the electromagnetic field is generated through the antenna, where the antenna is placed near the brain such that the targeted functional site of the brain is within the near field of the generated electromagnetic field and the extracellular fluid in the object functional site is polarized by the electric field of the near field, and the power of the near field is modulated to appear in bursts with the preset modulating frequency such that the polarization density of the extracellular fluid in the object functional site varies at the same frequency as the variation frequency of the power (i.e. the preset modulating frequency), thereby modulating the neuronal firing frequency at the targeted brain functional site.

In an example of the above method, the brain is transformed from its wake mode to its sleep mode, in which an antenna generates an electromagnetic field with its near field acting on the brain for sleep induction. During operation, the antenna is located near the brain and the sleep promoting sites of the brain, including the ventrolateral preoptic nucleus (VLPO), is within the near field of the generated electromagnetic field and the extracellular fluid in the object functional site is polarized by the power of the near field, where the power of the electromagnetic field is modulated with a low frequency in a burst format such that the polarization density of the extracellular fluid in the object functional site varies at the same frequency as the variation frequency of the power, thereby modulating the neuronal firing frequency at the brain sleep promoting site (including modulating the VLPO to a certain frequency), inducing the brain to transform from the wake mode to the sleep mode. Herein, the frequency of the generated electromagnetic field is determined such that the wavelength of the generated electromagnetic field in the sleep-promoting site in the brain best matches the dimensions of the sleep-promoting site so that the modulating effect of the generated electromagnetic field is selective to the sleep-promoting site. The frequency of the generated electromagnetic field is in the range of 1 GHz to 20 GHz, preferably in the range of 4 GHz to 6 GHz. The modulating frequency for the variation of the power of the generated electromagnetic field is in the range of 5 Hz to 2500 Hz, preferably in the range of 10 Hz to 30 Hz.

In another example of the above method for the treatment and prevention of Alzheimer's disease, an antenna generates an electromagnetic field with its near field acting on the brain, to implement two sequential steps of: 1) transforming the brain from its wake mode to its sleep mode to have the brain itself remove the waste generated by the neurons in the wake mode of the brain, through the brain's glymphatic system that is working effectively only in the brain's sleep mode; 2) transforming the brain from its wake mode to its sleep mode up the rapid eye movement (REM) sleep stage by modulating the brain sleep promoting site at the preset modulating frequency with the power provided by the near field; and 3) once the brain has reached the REM sleep stage in its sleep mode, modulating one or more other brain functional sites, especially the functional sites involved in learning and memory, with another particular modulating frequency different from the preset modulating frequency to facilitate the brain's natural process of having the neurons involved in consumption of certain proteins, such as amyloid beta, complete their consumption through substantially the same neuronal connecting networking environment as they were working during the brain wake mode in consuming the proteins. During the operation, the antenna is located near the brain and all the functional sites of the brain, especially the brain functional sites for sleep promoting and for learning and memorizing, are within the near field of the generated electromagnetic field and the extracellular fluid in all the brain functional sites is polarized by the near field, and the power of the near field is modulated with the low preset modulating frequency in a burst format such that the polarization densities of the extracellular fluid in the brain functional sites vary at the same frequency as the variation frequency of the power of the electromagnetic field, thereby modulating the neuronal firing frequency at the brain functional sites to the preset modulating frequency to transform the brain from wake mode to sleep mode, and then modulating the neuronal firing frequency to another frequency to facilitate the brain in its natural process of dealing with the left over proteins during the brain in wakefulness, which are the causes of Alzheimer's disease. The frequency of the generated electromagnetic field is determined such that the wavelength of the generated electromagnetic field in the sleep-promoting site best matches the dimensions of the sleep-promoting site as well as the learning and memorizing sites in the brain so that the modulating effect of the generated electromagnetic field is selective to the sleep-promoting site as well as the learning and memorizing sites. The frequency of the electromagnetic field is in the range of 1 GHz to 20 GHz, preferably in the range of 4 GHz to 6 GHz. The modulating frequency for the variation of the power of the generated electromagnetic field is in the range of 5 Hz to 2500 Hz, preferably in the range of 10 Hz to 30 Hz.

In another example of the above method, an antenna generates an electromagnetic field having power varying at the preset modulating frequency, with its near field acting on the brain. During the operation, the antenna is located near the brain and the part of the brain that is epileptically diseased is within the near field of the generated electromagnetic field and the extracellular fluid in this part of the brain is polarized by the near field; the power of the near field is modulated with a low frequency (i.e. the preset modulating frequency) in a burst format to make the polarization densities of the extracellular fluid in the brain functional sites vary at the same frequency as the variation frequency of the power, thereby modulating the neurons at the epileptically diseased part of the brain to fire at the normal frequency when this part of the brain is not epileptically diseased, until the epileptically diseased neurons have been rehabilitated to normal in their firing and the epilepsy is cured. The frequency of the generated electromagnetic field is determined such that the wavelength of the generated electromagnetic field at the epileptically diseased part of the brain best matches the dimensions of the epileptically diseased part of the brain so that the modulating effect of the generated electromagnetic field is selective to the epileptically diseased part of the brain. The frequency of the electromagnetic field is in the range of 200 MHz to 20 GHz. The modulating frequency for the variation of the power of the generated electromagnetic field is in the range of 1 Hz to 2500 Hz with the optimum in the range of 5 Hz to 45 Hz.

In another example of the above method to modulate the brain for treatment of depression, a current signal with its amplitude modulated at a low frequency is transferred to an antenna to generate an electromagnetic field with its near field acting on the brain functional sites that are responsible for serotonin (i.e. diminished activity of serotonin pathways plays a causal role in the pathophysiology of depression) release in the brain, including the subcallosal cingulate gyrus (SCG). During the operation, the antenna is located near the brain and the part of the brain that is responsible for serotonin release is within the near field of the generated electromagnetic field and the extracellular fluid in this part of the brain is polarized by the near field; the power of the near field is modulated with a low frequency in a burst format to make the polarization densities of the extracellular fluid in the brain functional sites vary at the same frequency as the variation frequency of the power, thereby modulating the neuronal firing frequency at the part of the brain to fire at the frequency they normally do when the brain is free of depression. In this way the neurons in the part of the brain are rehabilitated back to their normal firing behaviors and the depression in the brain is cured. Here, the frequency of the generated electromagnetic field is determined such that the wavelength of the generated electromagnetic field in the brain functional sites that are responsible for serotonin release in the brain best matches the dimensions of the brain functional sites, including the subcallosal cingulate gyrus (SCG) so that the modulating effect of the generated electromagnetic field is selective to these brain functional sites. The frequency of the electromagnetic frequency may be in the range of 1 GHz to 20 GHz. The modulating frequency for the variation of the power of the generated electromagnetic field is in the range of 1 Hz to 2500 Hz, preferably in the range of 5 Hz to 45 Hz.

In another example of the above method which is used to facilitate the brain in learning and memorizing, a current signal with its amplitude modulated at a low frequency is transferred to an antenna to generate an electromagnetic field with its near field acting on the brain functional sites that are responsible for learning and memorizing, including the frontal lobe and temporal lobe. During the operation, the antenna is placed near the concerned brain functional sites such that the brain functional sites are within the near field of the generated electromagnetic field and the extracellular fluid in this part of the brain is polarized by the near field; the power of the near field is modulated with a low frequency in a burst format to make the polarization densities of the extracellular fluid in the brain functional sites vary at the same frequency as the variation frequency of the power, thereby modulating all the neurons in the concerned brain functional sites to fire at a critical frequency for binding between the neurons via their synapses. With the modulation much more synapses of the neurons in the concerned brain functional sites are activated/alerted for binding such that the brain learns faster and memorizing more solidly. In the example, the frequency of the generated electromagnetic field is determined such that the wavelength of the generated electromagnetic field at the brain functional sites that are responsible for learning and memorizing best matches the dimensions of the brain functional sites so that the modulating effect of the generated electromagnetic field is selective to these brain functional sites. The frequency of the electromagnetic field is in the range of 200 MHz to 20 GHz, preferably in the range of 2 GHz to 10 GHz. The modulating frequency for the variation of the power of the generated electromagnetic field is in the range of 1 Hz to 2500 Hz, preferably in the range of 25 Hz to 85 Hz.

Likewise, the above method can be used for the treatment and prevention of insomnia.

As can be seen, the frequency (or the wavelength λ) of the generated electromagnetic field in vacuum is determined depending on the dimension of the targeted brain functional site, and the preset modulating frequency for modulating the power of the electromagnetic field is determined based on the operational neuronal firing frequency at the brain functional site and may be in the range of 1 Hz to 2500 Hz, preferably 5 Hz to 125 Hz, more preferably 5 Hz to 45 Hz, more preferably 25 Hz to 85 Hz, and more preferably 10 Hz to 30 Hz.

The method can be used for treatment and prevention of one or more of insomnia, Alzheimer's disease, epilepsy, and depression, or for facilitation of the brain in learning and memorizing.

In another embodiment, there is provided an apparatus of modulating a neuronal firing frequency at a brain functional site in a brain. Various examples of the apparatus are illustratively described below.

As shown in FIG. 2, an apparatus of the present embodiment, which is for example used for sleep induction, includes a signal generation module 21 and an antenna 23 connected to the signal generation module 21. The signal generation module 21 is configured to generate a current signal with its amplitude modulated with a preset low modulating frequency in a burst format 22 and send the current signal to the antenna 23. Therefore, the antenna 23 receives the modulated electrical signal from the signal generation module 21 and generates an electromagnetic field with its near field range 26 covering the sleep promoting site 24 of the brain 25, polarizing the extracellular fluid in the sleep promoting site 24 and inducing a variation of the polarization density at the modulating frequency such that the neuronal firing frequency is modulated to the modulated frequency for transforming the brain 25 from wake to sleep. Here, the electromagnetic field has power varying at the preset modulating frequency.

As shown in FIG. 3, an apparatus of the present embodiment, which is used for treatment and prevention of Alzheimer's disease, includes a signal generation module 31 and an antenna 33 connected to the signal generation module 31. The signal generation module 31 is configured to generate a current signal with its amplitude modulated with a preset low modulating frequency in a burst format 32 and send the current signal to the antenna 33. The antenna 33 receives the modulated electrical signal from the signal generation module 31 and generates an electromagnetic field with its near field range 36 covering the sleep promoting site 34 and the learning and memorizing sites 34' as well as other sites of the brain 35, thereby firstly polarizing the extracellular fluid in the brain functional sites and inducing variation of the polarization density at the brain functional sites with the preset modulating frequency such that the neuronal firing at the sleep promoting site 34 is modulated to transform the brain 35 from wake to sleep to facilitate the glymphatic system removal of waste generated by the neurons in the brain 35; and then, as the brain 35 is in its sleep mode, inducing the polarization density at the learning and memorizing sites 34' as well as other sites of the brain 35 to vary at another particular frequency such that the neuronal firing at the learning and memorizing sites 34' as well as other sites of the brain 35 is modulated to the another particular frequency that facilitates synaptic connections between the neurons in consumption/absorption of the leftover proteins from the wake mode of the brain 35; both of these facilitation processes provide the effect of treatment and prevention of Alzheimer's disease to the brain 35.

Figure 4:
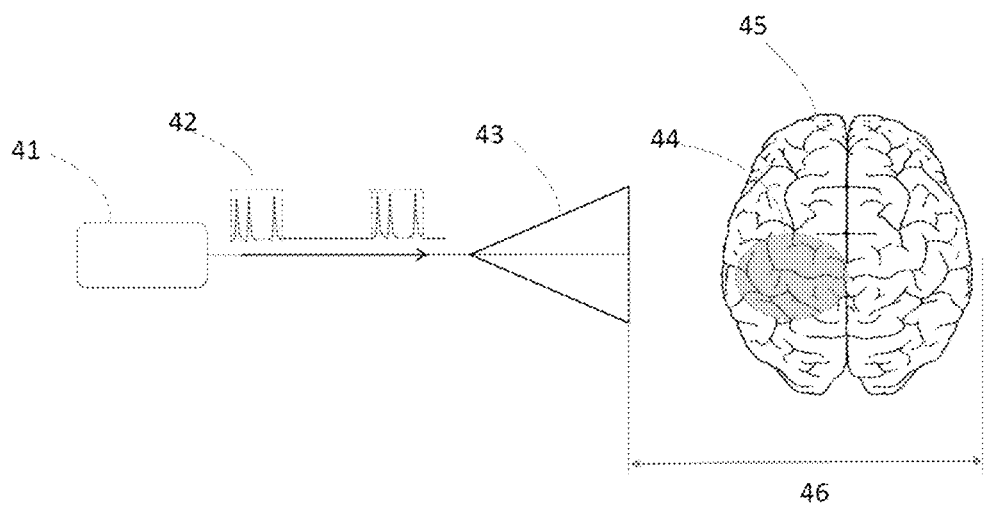
FIG. 4 schematically shows an apparatus of modulating a neuronal firing frequency at a brain functional site in a brain, in which a signal generation module generates and sends an electrical signal, e.g. a current signal with its amplitude modulated at a low frequency, to an antenna to generate an electromagnetic field with its near field acting on the brain to modulate the brain for treatment of epilepsy, according to another embodiment of the present invention.

As shown in FIG. 4, an apparatus of the present embodiment, which is used for treatment of epilepsy, includes a signal generation module 41 and an antenna 43 connected to the signal generation module 41. The signal generation module 41 is configured to generate a current signal with its amplitude modulated with a preset low modulating frequency in a burst format 42 and send the current signal to the antenna 43. The antenna 43 receives the modulated electrical signal from the signal generation module 41 and generates an electromagnetic field with its near field range 46 covering the epileptically diseased part 44 of the brain 45, thereby polarizing the extracellular fluid in the epileptically diseased part 44 of the brain 45 and inducing a variation of the polarization density at the modulating frequency that is the normal neuronal firing frequency for this part 44 of the brain 45 when it is not epileptically diseased to modulate the neurons in the epileptically diseased part 44 to fire at the modulating frequency such that the neurons are rehabilitated to normal in their neuronal firing behavior and the epilepsy in the brain 45 is cured.

Figure 5:
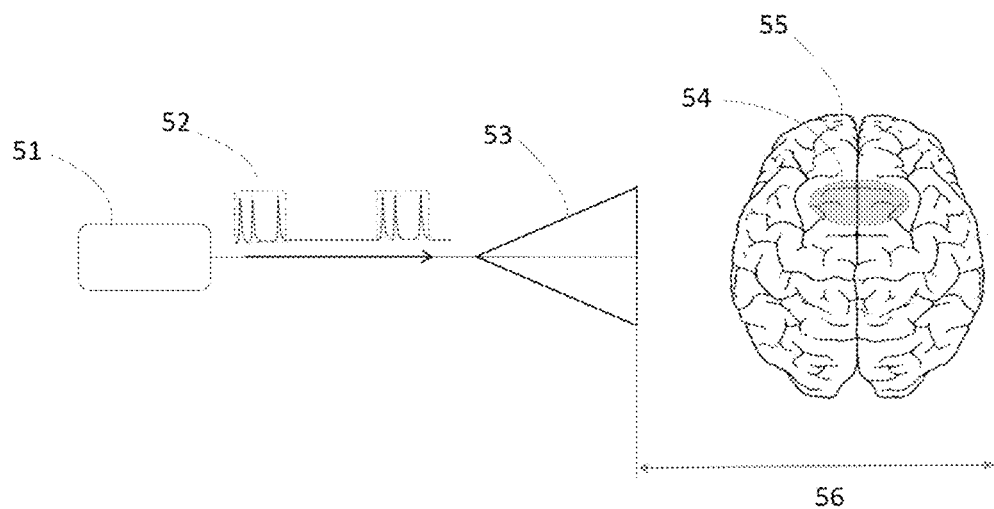
FIG. 5 schematically shows an apparatus of modulating a neuronal firing frequency at a brain functional site in a brain, in which a signal generation module generates and sends an electrical signal, e.g. a current signal with its amplitude modulated at a low frequency, to an antenna to generate an electromagnetic field with its near field acting on the brain functional sites that are responsible for serotonin release in the brain, including the SCG, to modulate the brain for treatment of depression, according to another embodiment of the present invention.

As shown in FIG. 5, an apparatus of the present embodiment, which is used for treatment of depression, includes a signal generation module 51 and an antenna 53 connected to the signal generation module 51. The signal generation module 51 is configured to generate a current signal with its amplitude modulated with a preset low modulating frequency in a burst format 52 and send the current signal to the antenna 53. The antenna 53 receives the modulated electrical signal from the signal generation module 51 and generates an electromagnetic field with its near field range 56 covering the brain functional sites that are responsible for serotonin release in the brain 55, including the SCG 54, thereby polarizing the extracellular fluid in the SCG 54 as well as the brain functional sites that are responsible for serotonin release in the brain 55, and inducing a variation of the polarization density at the modulating frequency that is the normal firing frequency of these brain functional sites when the brain 55 is free of depression, rehabilitating the neurons in these brain functional sites to their normal firing behaviors such that the depression in the brain 55 is cured.

Figure 6:
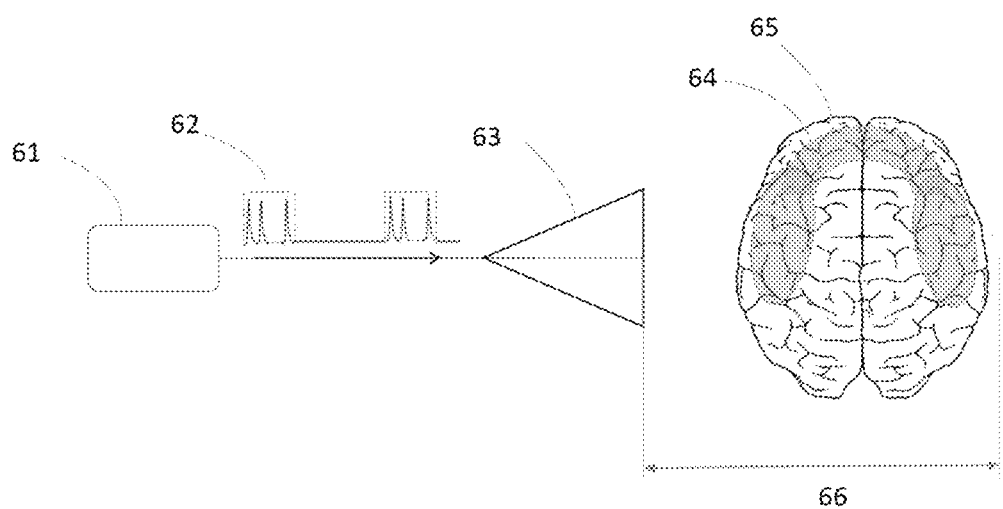
FIG. 6 schematically shows an apparatus of modulating a neuronal firing frequency at a brain functional site in a brain, in which a signal generation module generates and sends an electrical signal, e.g. a current signal with its amplitude modulated at a low frequency, to an antenna to generate an electromagnetic field with its near field acting on the brain functional sites that are responsible for learning and memorizing, including the frontal lobe and temporal lobe, to facilitate the brain in learning and memorizing, according to another embodiment of the present invention.

As shown in FIG. 6, an apparatus of the present embodiment, which is used for treatment of depression, includes a signal generation module 61 and an antenna 63 connected to the signal generation module 61. The signal generation module 61 is configured to generate a current signal with its amplitude modulated with a preset low modulating frequency in a burst format 62 and send the current signal to the antenna 63. The antenna 63 receives the modulated electrical signal from the signal generation module 61 and generates an electromagnetic field with its near field range 66 covering the learning and memorizing sites 64 as well as other brain functional sites in the brain 65, polarizing the extracellular fluid in the learning and memorizing sites 64 as well as other brain functional sites in the brain 65, and inducing a variation of the polarization density at a modulating frequency to modulate all the neurons in the concerned brain functional sites fire at a critical frequency for binding between the neurons via their synapses, activating much more than usual the synapses of the neurons in the concerned brain functional sites for binding such that the brain 65 learns faster and memorizing more solidly.

As to the apparatus in the above examples, the near field of the electromagnetic field satisfies the condition of $$0 < d \leq 0.62 * \sqrt{\frac{D^3}{\lambda}},$$

wherein d represents the distance from the antenna to an edge of the near field where the near field ends, D represents the largest dimension of the antenna, and λ represents the wavelength of the generated electromagnetic field in vacuum.

The wavelength λ of the generated electromagnetic field in vacuum is such that the wavelength of the electromagnetic field at the brain functional site matches the dimension of the brain functional site.

Additionally or alternatively, the wavelength λ of the generated electromagnetic field in vacuum is such that the wavelength of the electromagnetic field at the brain functional site is from 70% to 130% of the dimension of the brain functional site.

The preset modulating frequency is determined based on the operational (or normal) neuronal firing frequency at the brain functional site and is preferably in the range of 1 Hz to 2500 Hz, preferably 5 Hz to 125 Hz, more preferably 5 Hz to 45 Hz, more preferably 25 Hz to 85 Hz, and more preferably 10 Hz to 30 Hz.

Sensing/Detecting of Neuronal Firing Frequency

Hereinafter, sensing of neuronal firing frequency is described below with reference to FIGS. 7-11.

Figure 7:
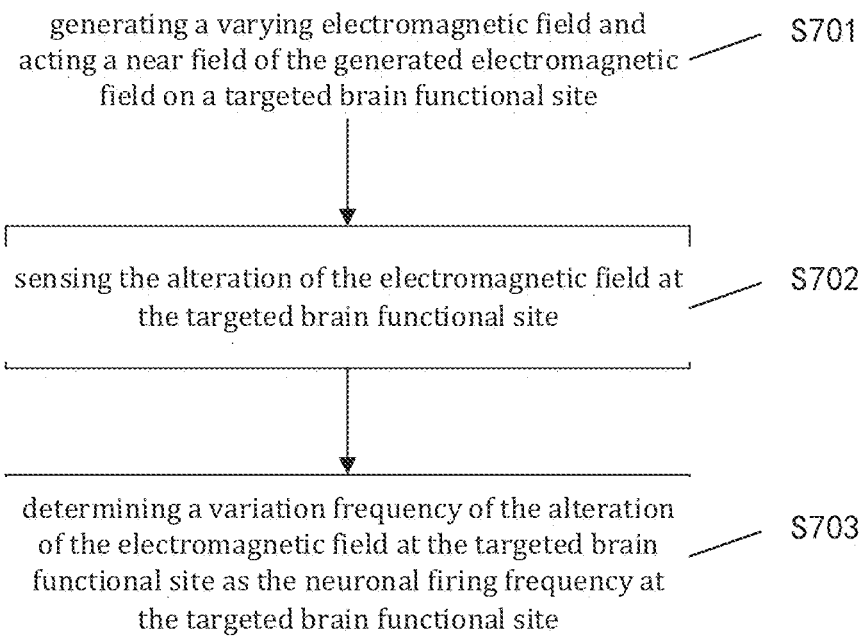
FIG. 7 is a schematic diagram showing a method of actively sensing a neuronal firing frequency at a functional site in a brain according to an embodiment of the present invention.

In another embodiment of the present invention, as shown in FIG. 7, a method of actively sensing a neuronal firing frequency at a functional site in a brain includes:

S701: generating a varying electromagnetic field and acting a near field of the generated electromagnetic field on a targeted brain functional site;

S702: sensing the alteration of the electromagnetic field at the targeted brain functional site; and S703: determining a variation frequency of the alteration of the electromagnetic field at the targeted brain functional site as the neuronal firing frequency at the targeted brain functional site.

Here the near field is defined by the distance d of the generated varying electromagnetic field from the antenna, the largest dimension D of the antenna, as well as the wavelength λ of the electromagnetic field generated by the antenna in vacuum in the following relationship:

$$0 < d \leq 0.62 * \sqrt{\frac{D^3}{\lambda}}$$

For example, in the case of selectively modulating the sleep promoting site ventrolateral preoptic nucleus (VLPO) in the brain, given that the dimension of the VLPO is about 1 cm and an electromagnetic field of 6 cm wavelength in vacuum will have a wavelength of 1 cm in the brain, the 1 cm wavelength matches the dimension of the VLPO for high modulation efficiency. In this case, the wavelength λ of the electromagnetic field is 6 cm and thus the frequency of the electromagnetic field is 5 GHz, and the largest dimension D of the antenna is 18 cm, then $$0 < d \leq 0.62 * \sqrt{\frac{18^3}{6}} = 19.3 \text{ cm}$$

That is, the maximum distance of the near field is 19.3 cm from the antenna. Here, the value of the dimension D relates to the value of the distance d, and those skilled in the art knows proper adjustment of the values of D and d correlatively to properly acting the targeted brain functional site.

Through the strong inductive and capacitive effect of the currents and charges in the antenna, the near field of the generated electromagnetic field induces the neuronal clusters formed by groups of neurons in the brain to act as the secondary antennas, thereby inducing an electric field in the brain, which polarizes the extracellular fluid in the targeted brain functional site. As a result of polarization of the extracellular fluid in the targeted brain functional site by the near field, the power of the near field is taken by the extracellular fluid in the targeted brain functional site in building the polarization density of the extracellular fluid, and the phase and amplitude of the waves of the electromagnetic field, including the near field, are altered, with the level of alteration depending on the level of the polarization density of the extracellular fluid, which varies with the concentration of the charged particles in the extracellular fluid. At the meantime, the neurons in the extracellular fluid at the brain site fire at a certain frequency, thereby varying the concentration of the charged particles in the extracellular fluid at the neuronal firing frequency and thus varying the polarization density of the extracellular fluid at the neuronal firing frequency, such that the alteration of the phase and amplitude of the waves of the electromagnetic field in the brain, including the near field, varies at the neuronal firing frequency relative to the generated electromagnetic field.

In the present invention, the neuronal firing frequency at a brain functional site is actively sensed with the generated varying electromagnetic field having its near field surrounding the targeted brain functional site and polarizing the extracellular fluid at the brain functional site, and by measuring the variation frequency of the alteration of the electromagnetic field in association with the alteration of the polarization density of the extracellular fluid at the brain functional site, in which the polarization density of the extracellular fluid is induced by the electromagnetic field and is varied by the firing of the neurons at the brain functional site through varying the concentration of the charged particles in the extracellular fluid. By using a predetermined calibration of the sensed frequency in relation to the state or characteristics of the targeted brain functional site, the functional activity at the targeted brain functional site is sensed. In the method of the present invention, the frequency of the generated electromagnetic field in vacuum is in the range of 200 MHz to 150 GHz, with the optimum as such that the wavelength of the generated electromagnetic field in the brain matches the dimension of the targeted brain functional site. The measurement for the variation frequency of the alteration of the electromagnetic field in association with the alteration of the polarization density of the extracellular fluid at the brain functional site includes measuring the alteration of the phase of the sensed electromagnetic field (relative to the generated electromagnetic field) in association with the alteration of the polarization density of the extracellular fluid at the brain functional site, and/or includes measuring the alteration of the amplitude of the sensed electromagnetic field (relative to the generated electromagnetic field) in association with the alteration of the polarization density of the extracellular fluid at the brain functional site. Then the frequency of such alteration can be calculated.

Preferably, the frequency of the generated varying electromagnetic field in vacuum is such that the wavelength of the electromagnetic field at the brain functional site matches the dimension of the targeted brain functional site.

The waveform of the varying electromagnetic field may be alternating or pulsed, or the power of the varying electromagnetic field is varying at a preset modulated frequency.

The alteration of the electromagnetic field in the targeted brain functional site may be a phase alteration and is determined by comparing the phase of the sensed electromagnetic field at the brain functional site with the phase of the generated electromagnetic field, or the alteration of the electromagnetic field in the targeted brain functional site is an amplitude alteration and is determined by comparing the amplitude of the sensed electromagnetic field at the brain functional site with the amplitude of the generated electromagnetic field.

The alteration of the electromagnetic field at the targeted brain functional site may be sensed by the antenna or alternatively by an antenna separate from the antenna that generates the electromagnetic field acting on the brain functional site.

The functional site in the brain may be, for example, the anterior cingulate cortex (ACC) for pain perception, and the degree of pain percept in the brain is determined from the determined neuronal firing frequency at the ACC together with a calibration between the neuronal firing frequency and an intensity of pain.

The functional site in the brain may be, for example, the brain site for intention to act, including the prefrontal cortex and motor cortex.

The functional site in the may be any functional site in the brain according to the specific applications of the method of the present invention, including but not limited to a functional site in the hindbrain, in the midbrain, in the forebrain, in the neural pathways, in the neuroendocrine systems, in the neurovascular systems, in the dural meningeal system, or in the reticular formation.

In another embodiment of the present invention, as shown in FIGS. 8-11, there is provided an apparatus of actively sensing a neuronal firing frequency at a functional site in a brain, including a signal generation module (81, 91, 101, 111), an antenna (83, 93, 103, 113) connected to the signal generation module (81, 91, 101, 111), and a computing module (810, 910, 1010, 1110).

The signal generation module (81, 91, 101, 111) is configured to generate and send a varying current signal (82, 92, 102, 112) to the antenna (83, 93, 103, 113) for generating a varying electromagnetic field, a near field of which is used for acting on a targeted brain functional site (104, 114, 114') in the brain (85, 95, 105, 115).

The antenna 93 may be further configured to sense the alteration of the electromagnetic field at the targeted brain functional site, or the apparatus further includes a separate antenna (88, 108, 118) configured to sense the alteration of the electromagnetic field at the targeted brain functional site.

The computing module (810, 910, 1010, 1110) is configured to determine, based on the sensed alteration of the electromagnetic field at the targeted brain functional site, a variation frequency of the alteration of the electromagnetic field at the targeted brain functional site as the neuronal firing frequency at the targeted brain functional site.

As can be seen from the above, the electrical signal (82, 92, 102, 112) for generating the varying electromagnetic field is compared with an electrical signal (89, 99, 109, 119) generated from the sensed electromagnetic field at the targeted brain functional site to determine the variation frequency of the alteration (or difference) between the electrical signal (82, 92, 102, 112) and the electrical signal (89, 99, 109, 119).

The near field is defined by the distance d of the generated varying electromagnetic field from the antenna generating the electromagnetic field, the largest dimension D of the antenna, as well as the wavelength λ of the generated electromagnetic field in vacuum in the relationship of $$0 < d \le 0.62 * \sqrt{\frac{D^3}{\lambda}}.$$

The frequency of the generated varying electromagnetic field in vacuum is such that the wavelength of the electromagnetic field at the brain functional site matches the dimension of the targeted brain functional site.

The waveform of the varying electromagnetic field is alternating or pulsed, or the power of the varying electromagnetic field is varying at a preset modulated frequency.

The alteration of the electromagnetic field in the targeted brain functional site may be a phase alteration and is determined by comparing the phase of the sensed electromagnetic field at the brain functional site with the phase of the generated electromagnetic field, or the alteration of the electromagnetic field in the targeted brain functional site may be an amplitude alteration and is determined by comparing the amplitude of the sensed electromagnetic field at the brain functional site with the amplitude of the generated electromagnetic field.

An example of the apparatus for the implementation of the above method of the present invention is for sensing the pain percept in the brain, in which a signal generation module generates an alternating or pulsed current signal of a certain frequency and passes the current signal to an antenna, which in turn generates a varying electromagnetic field with its near field acting on the brain functional site for pain perception, including the ACC, and the alteration of the near field at the brain functional site is detected with the antenna or another antenna by comparing the originally generated electromagnetic field and the detected electromagnetic field at the brain functional site, and further the frequency of such alteration (e.g. alterations in phase, amplitude, etc.) is calculated by a computing module. The alterations include an alteration in the phase of the electromagnetic field and an alteration in the amplitude of the electromagnetic field. The frequency of the generated electromagnetic field may be in the range of 200 MHz to 30 GHz with the optimum from 3 GHz to 8 GHz, so that the wavelength of the generated electromagnetic field at the brain functional site matches the dimension of the brain functional site. When the sensed variation frequency of the alterations between the generated electromagnetic field and the sensed electromagnetic field is above 28 Hz, the pain percept in the brain is detected. With a calibration of the sensed frequency in relation to the intensity of pain, the degree of pain percept in the brain is sensed.

Another example of the apparatus for the implementation of the above method of the present invention is to sense the intention to act in a brain for a brain-machine interface, in which a signal generation module generates and sends a current signal to an antenna which in turn generates a varying electromagnetic field with its near field acting on the brain functional site for intention to act, including the prefrontal cortex and motor cortex, also, the alteration of the electromagnetic field at the brain functional site is sensed by the same antenna or a separate antenna, and then the originally generated electromagnetic field and the sensed electromagnetic field at the brain functional site are compared over time for obtaining the alteration between these two electromagnetic fields and further determining the variation frequency of such alterations as the neuronal firing frequency at the brain functional site. The frequency of the generated electromagnetic field is in the range of 200 MHz to 30 GHz with the optimum from 1 GHz to 8 GHz. The sensed neuronal firing frequency is then interpreted, based on the functional characteristics of the firing frequency of the neurons in the functional site, as the signal for a brain-machine interface in controlling a machine or a system directly by the brain.

In the present invention, in order to actively sense the neuronal firing frequency at a brain functional site, a varying electromagnetic field is generated, with its near field inducing an electric field at the brain functional site and polarizing the extracellular fluid at the brain functional site, meanwhile the electromagnetic field past through the brain functional site is received with another antenna, or the electric field induced by the generated electromagnetic field at the brain functional site is sensed with the same antenna for generating the varying electromagnetic field, and then the received electromagnetic field or the sensed electric field is compared with the originally generated field to determine the variation frequency of the alteration between the received electromagnetic field or the sensed electric field and the originally generated field for determining the neuronal firing frequency at the brain functional site. Alternatively, the comparison of the fields can be equivalently performed by the comparison of the electrical signal for generating the field and the electrical signal generated from the sensed/received field.

Figure 8:
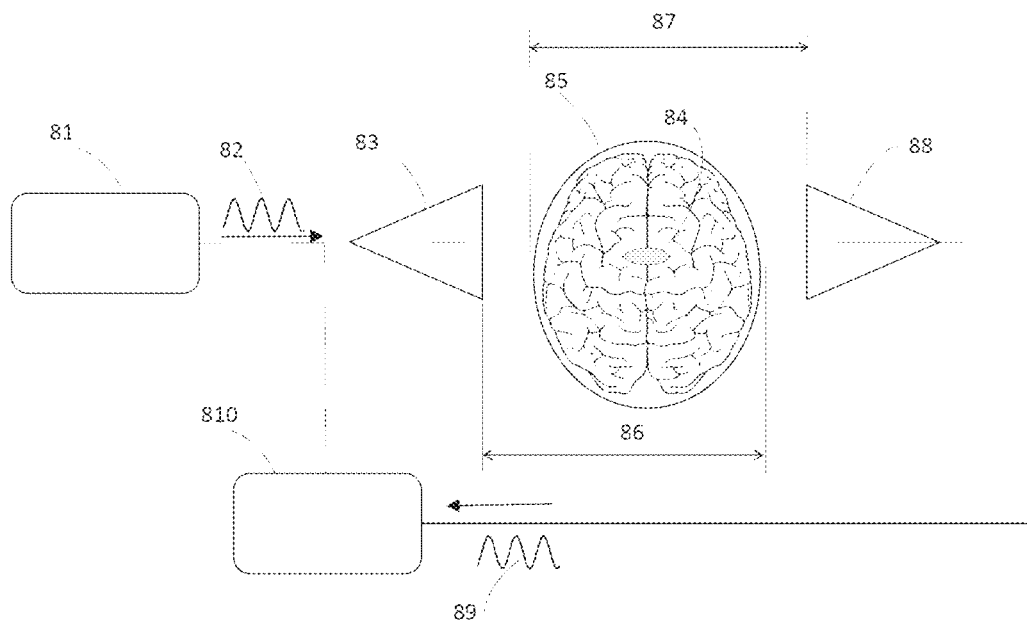
FIG. 8 shows an embodiment of the present invention, in which in order to sense the neuronal firing frequency of a functional brain site in a brain, a varying electromagnetic field is generated with its near field acting on the functional site in the brain, another antenna is arranged to receive the generated electromagnetic field past through the brain functional site, and the received electromagnetic field is compared with the originally generated electromagnetic field to determine the variation frequency of the alterations between these two electromagnetic fields for determining the neuronal firing frequency at the brain functional site.

Some example are further described below with reference to FIGS. 8-11. As shown in FIG. 8, for sensing the neuronal firing frequency at a functional site 84 in a brain 85, a signal generation module 81 generates and passes a varying current signal 82 to an antenna 83 to generate an electromagnetic field with its near field within the distance range 86, inducing an electric field at the brain functional site 84; another antenna 88 is placed within the near field range 87 to receive the electromagnetic field past through the brain functional site 84 and passes the received field signal 89 to the computing module 810, where the received field signal 89 is compared with the original signal 82 for generating the field from the signal generation module 81 to determine the variation frequency of the alteration between the received field and the originally generated field for determining the neuronal firing frequency at the brain functional site 84.

Figure 9:
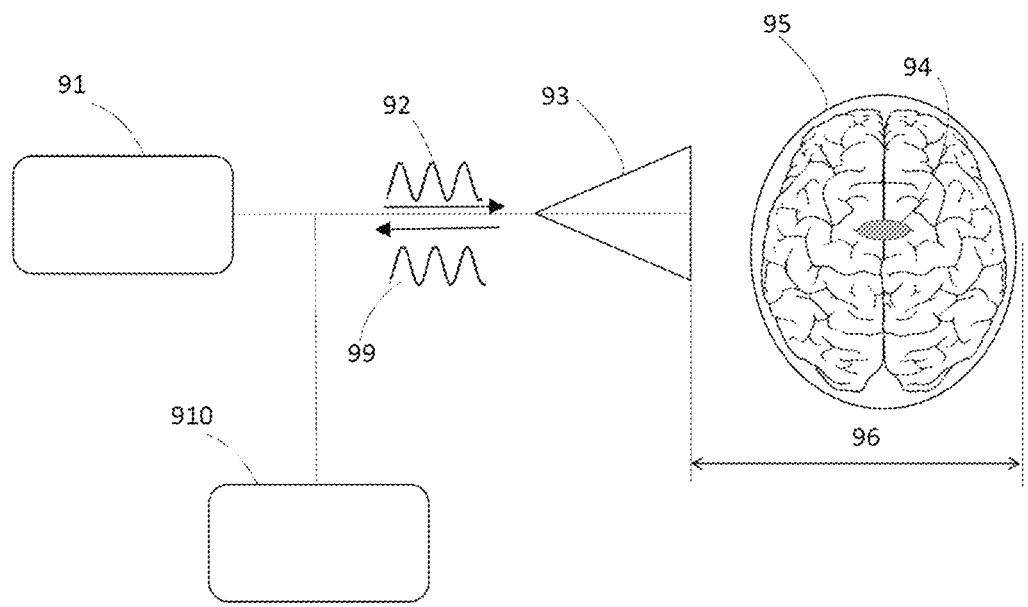
FIG. 9 shows an embodiment of the present invention, in which in order to sense the neuronal firing frequency of a functional brain site in a brain, a varying electromagnetic field is generated with its near field acting on the functional site in the brain, and the same antenna senses the electric field induced by the generated electromagnetic field at the brain functional site, and the sensed induced field is compared with the originally generated field to determine the variation frequency of the alterations between the two fields for determining the neuronal firing frequency at the brain functional site.

As shown in FIG. 9, for sensing the neuronal firing frequency at a functional site 94 in a brain 95, a signal generation module 91 generates and passes a varying current signal 92 to an antenna 93, which in turn generates a varying electromagnetic field with its near field within the distance range 96, thereby inducing an electric field at the brain functional site 94. Meanwhile, the antenna 93 further senses the electric field induced by the generated electromagnetic field at the brain functional site 94 and passes the sensed signal to the computing module 910, which compares the sensed induced field signal 99 with the signal 92 for originally generating the field from the signal generation module 91 to determine the variation frequency of the alteration between the two sensed field and the generated field, for determining the neuronal firing frequency at the brain functional site.

Figure 10:
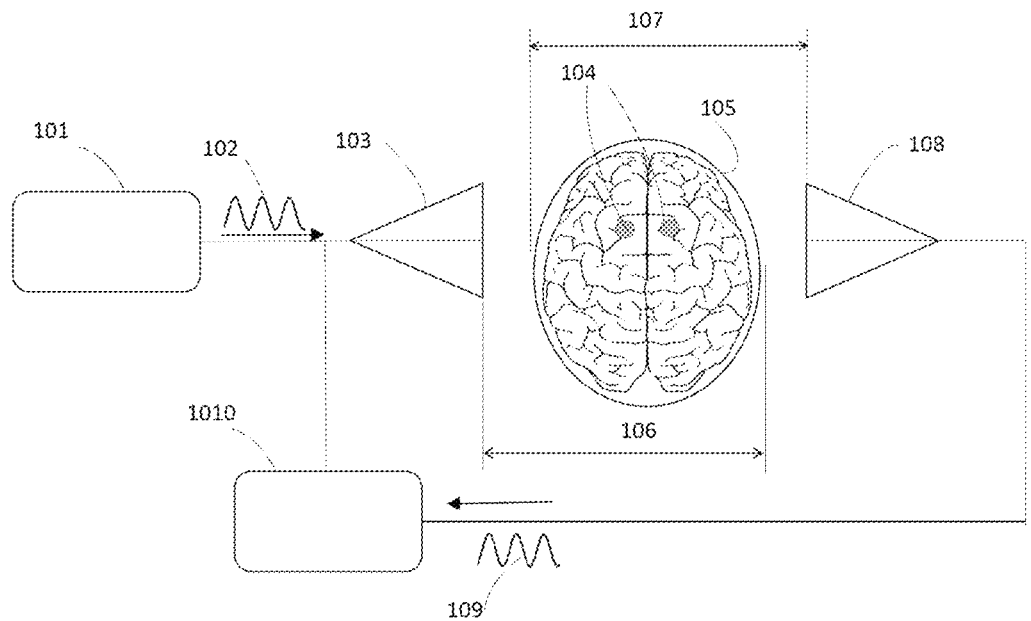
FIG. 10 shows an embodiment of the present invention, in which in order to sense the neuronal firing frequency of a functional brain site in a brain, a varying electromagnetic field is generated with its near field acting on the brain functional site for pain perception, i.e. the ACC, meanwhile another antenna is arranged to receive the generated electromagnetic field past through the brain functional sites, and the received electromagnetic field is compared with the originally generated electromagnetic field to determine the variation frequency of the alterations between these two fields for determining the neuronal firing frequency at the brain functional site.

As shown in FIG. 10, for sensing the neuronal firing frequency at the pain perception functional site ACC 104 of a brain 105, a signal generation module 101 generates and passes a varying current signal 102 to an antenna 103 to generate an electromagnetic field with its near field within the distance range 106, thereby inducing an electric field at the brain site ACC 104; meanwhile, another antenna 108 is placed within the near field range 107 to receive the electromagnetic field past through the brain site ACC 104 and passes the received field signal 109 to a computing module 1010, which compares the received field signal 109 with the original signal 102 for generating the field from the signal generation module 101, to determine the variation frequency of the alteration between the received field and the originally generated field for determining the neuronal firing frequency at the brain functional site 104. The degree of pain percept in the brain 105 is determined from the sensed neuronal firing frequency at the pain perception site ACC with a predetermined calibration between the frequency and intensity of pain.

Figure 11:
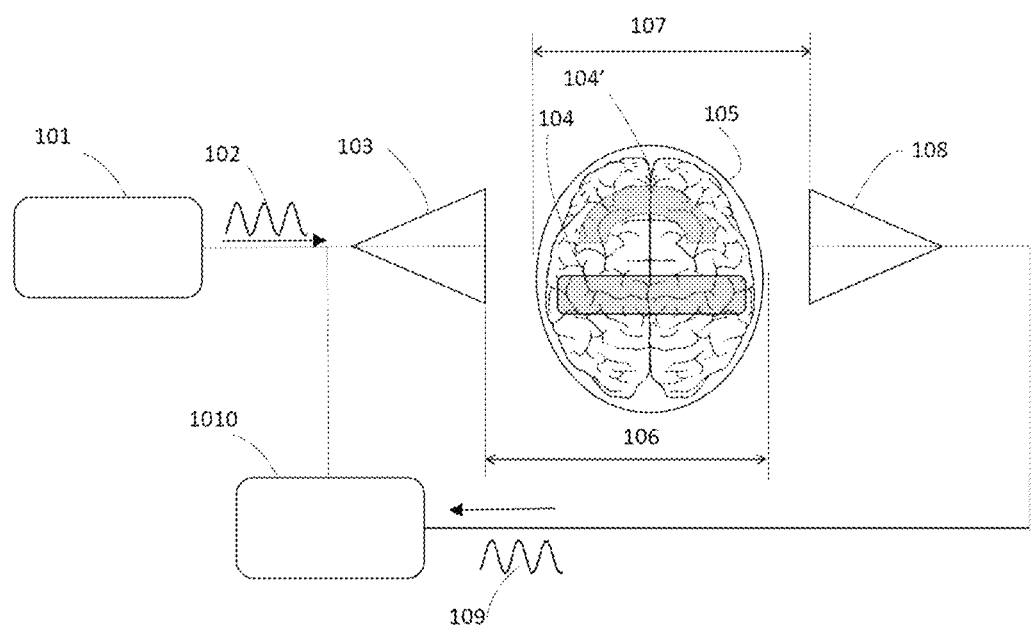
FIG. 11 shows an embodiment of the present invention, in which in order to sense the neuronal firing frequency at the brain functional site related to intention to act for a brain-machine interface, a varying electromagnetic field is generated with its near field acting on the brain functional site, the prefrontal cortex and motor cortex, meanwhile another antenna is arranged to receive the electromagnetic field at the brain functional site, generate an electrical signal based on the received electromagnetic field and sends the electrical signal to a computing module, in which the electrical signal used for originally generating the electromagnetic field and the signal based on the received electromagnetic field at the brain functional site are compared to determine the variation frequency of the alterations between the two electromagnetic fields for determining the neuronal firing frequency at the brain functional site, and then the sensed neuronal firing frequency is interpret for a brain-machine interface.

As shown in FIG. 11, for sensing the neuronal firing frequency at the prefrontal cortex 114 and motor cortex 114' of a brain 115, a signal generation module 111 generates and passes a varying current signal 112 to an antenna 113 to generate an electromagnetic field with its near field within the distance range 116, thereby inducing an electric field at the brain functional site including the prefrontal cortex 114 and motor cortex 114'; meanwhile, another antenna 118 is placed within the near field range 117 to receive the electromagnetic field at the brain functional site including the prefrontal cortex 114 and motor cortex 114' and pass the received field signal 119 to a computing module 1110, which compares the received the field signal 119 with the original signal 112 for generating the field from the signal generation module 111 to determine the variation frequency of the alteration between the received field and the generated field for determining the neuronal firing frequency at the brain functional site including the prefrontal cortex 114 and motor cortex 114', and then the sensed neuronal firing frequency is interpret for a brain-machine interface.

In the above embodiments of the present invention, the waveform of the electromagnetic field generated by the antenna may be of any waveform, including but not limited to alternating waveform and pulse waveform.

While the invention is susceptible to various modifications and alternative forms, specific embodiments thereof have been shown by way of example in the drawings and the above detailed description. It should be understood, however, that it is not intended to limit the invention to the particular forms disclosed, but on the contrary, the intention is to cover all modifications, equivalents, and alternatives falling within the spirit and scope of the invention as defined by the appended claims.

It is expected that during the life of a patent maturing from this application many relevant disinfecting connectors will be developed; the scope of the term disinfecting connector is intended to include all such new technologies a priori.

The terms "comprises", "comprising", "includes", "including", "has", "having" and their conjugates mean "including but not limited to".

As used herein, the singular forms "a", "an" and "the" include plural references unless the context clearly dictates otherwise.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The invention claimed is:

1. A method of actively sensing a neuronal firing frequency at a functional site in a brain, comprising:
   generating a varying electromagnetic field and acting a near field of the generated electromagnetic field on a targeted brain functional site;
   sensing alteration of the electromagnetic field at the targeted brain functional site; and
   determining a variation frequency of the alteration of the electromagnetic field at the targeted brain functional site as the neuronal firing frequency at the targeted brain functional site,
   wherein the near field is defined by the distance d of the generated varying electromagnetic field from an antenna generating the electromagnetic field, the largest dimension D of the antenna, as well as the wavelength $\lambda$ of the generated electromagnetic field in vacuum in the relationship of $$0 < d \le 0.62 * \sqrt{\frac{D^3}{\lambda}}.$$

2. The method of claim 1, wherein the frequency of the generated varying electromagnetic field in vacuum is such that the wavelength of the electromagnetic field at the brain functional site matches a dimension of the targeted brain functional site.

3. The method of claim 1, wherein the waveform of the varying electromagnetic field is alternating or pulsed.

4. The method of claim 1, wherein,
   the alteration of the electromagnetic field in the targeted brain functional site is a phase alteration and is determined by comparing the phase of the sensed electromagnetic field at the brain functional site with the phase of the generated electromagnetic field, or
   the alteration of the electromagnetic field in the targeted brain functional site is an amplitude alteration and is determined by comparing the amplitude of the sensed electromagnetic field at the brain functional site with the amplitude of the generated electromagnetic field.

5. The method of claim 1, wherein the alteration of the electromagnetic field at the targeted brain functional site is sensed by a first antenna generating the electromagnetic field acting on the brain functional site or by a second antenna separate from the first antenna.

6. The method of claim 1, wherein the functional site in the brain is the anterior cingulate cortex (ACC) for pain perception, and a degree of pain percept in the brain is determined from the determined neuronal firing frequency at the ACC together with a calibration between the neuronal firing frequency and an intensity of pain.

7. The method of claim 1, wherein the functional site in the brain is the brain site for intention to act, including the prefrontal cortex and motor cortex.

8. An apparatus for actively sensing a neuronal firing frequency at a functional site in a brain, comprising:
   means for generating a varying electromagnetic field and acting a near field of the generated electromagnetic field on a targeted brain functional site;
   means for sensing alteration of the electromagnetic field at the targeted brain functional site; and
   means for determining a variation frequency of the alteration of the electromagnetic field at the targeted brain functional site as the neuronal firing frequency at the targeted brain functional site,
   wherein the near field is defined by the distance d of the generated varying electromagnetic field from an antenna generating the electromagnetic field, the largest dimension D of the antenna, as well as the wavelength $\lambda$ of the generated electromagnetic field in vacuum in the relationship of $$0 < d \le \sqrt{\frac{D^3}{\lambda}},$$

9. The apparatus of claim 8, wherein the frequency of the generated varying
   electromagnetic field in vacuum is configured such that the wavelength of the electromagnetic field at the
   brain functional site matches the dimension of the targeted brain functional site.

10. The apparatus of claim 8, wherein the waveform of the varying
    electromagnetic field is alternating or pulsed, or the power of the varying electromagnetic field is
    varying at a preset modulated frequency.

11. The apparatus of claim 8, wherein:
    the alteration of the electromagnetic field in the targeted brain functional site is a phase alteration and is determined by comparing the phase of the sensed electromagnetic field at the
brain functional site with the phase of the generated electromagnetic field, or
the alteration of the electromagnetic field in the targeted brain functional site is an
amplitude alteration and is determined by comparing the amplitude of the sensed electromagnetic field at the brain functional site with the amplitude of the generated electromagnetic field.

* * * * *